US010196600B2

(12) United States Patent
Bai et al.

(10) Patent No.: US 10,196,600 B2
(45) Date of Patent: Feb. 5, 2019

(54) METHOD FOR MANUFACTURING AN ACTIVE SUBSTANCE FOR INDUCING SELF-LYSIS IN MICROALGA CELLS, ACTIVE SUBSTANCE OBTAINED THEREFROM, AND METHOD FOR INDUCING SELF-LYSIS IN MICROALGA CELLS

(71) Applicant: Industrial Technology Research Institute, Hsinchu (TW)

(72) Inventors: Ming-Der Bai, Hemei Township (TW); Chung-Cheng Han, Taipei (TW); Wen-Chang Lu, Hsinchu (TW); Hou-Peng Wan, Taoyuan (TW); Jo-Shu Chang, Taichung (TW); Chun-Yen Chen, Tainan (TW); Hsin-Yueh Chang, Tainan (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 14/736,363

(22) Filed: Jun. 11, 2015

(65) Prior Publication Data

US 2016/0177256 A1 Jun. 23, 2016

(30) Foreign Application Priority Data

Dec. 18, 2014 (TW) ............................ 103144255 A

(51) Int. Cl.
*C12N 1/06* (2006.01)
*C12N 1/20* (2006.01)
*C12P 1/04* (2006.01)
*C12R 1/07* (2006.01)

(52) U.S. Cl.
CPC ................ *C12N 1/06* (2013.01); *C12N 1/20* (2013.01); *C12P 1/04* (2013.01); *C12R 1/075* (2013.01)

(58) Field of Classification Search
CPC ............... C12N 1/06; C12N 1/20; C12N 1/04
USPC ........................................................ 435/170
See application file for complete search history.

(56) References Cited

U.S. PATENT DOCUMENTS

| | | | | |
|---|---|---|---|---|
| 7,935,515 | B2 | 5/2011 | Franklin et al. | |
| 7,951,913 | B2 * | 5/2011 | Varga | C07K 7/62 530/319 |
| 8,288,150 | B2 | 10/2012 | Chuu et al. | |
| 8,450,111 | B2 | 5/2013 | Salvo et al. | |
| 2009/0269839 | A1 | 10/2009 | Oyler | |
| 2011/0117059 | A1 | 5/2011 | Deremaux et al. | |
| 2013/0040340 | A1 | 2/2013 | Dauner et al. | |
| 2014/0045217 | A1 | 2/2014 | Milos et al. | |

FOREIGN PATENT DOCUMENTS

| | | | |
|---|---|---|---|
| CN | 102286381 | A | 12/2011 |
| CN | 103045709 | A | 4/2013 |
| CN | 103173273 | A | 6/2013 |
| TW | 201144435 | A1 | 12/2011 |
| WO | WO 2012/089842 | A2 | 7/2012 |
| WO | WO 2013/110539 | A2 | 8/2013 |
| WO | WO 2014/120989 | A1 | 8/2014 |

OTHER PUBLICATIONS

J.A. Sogn. Structure of the Peptide Antibiotic Polypeptin. Journal of Medicinal Chemistry (1976), v19(10), p. 1228-1231.*
Raddadi et al. The autolytic phenotype of the Bacillus cereus group. Journal of Applied Microbiology (2005), v99, p. 1070-1081.*
Hathout et al. Kurstakins: A New Class of Lipopeptides Isolated from Bacillus thuringiensis. Journal of Natural Products (2000), v63, p. 1492-1496.*
Paulus et al. The Biosynthesis of Polymyxin B by growing cultures of Bacillus polymyxa. Journal of Biological Chemistry (1964), v264(3), p. 865-871.*
H.D.B Jenkins. Clausius-Clapeyron Equation Chapter 26 in Chemical Thermodynamics at a Glance (2008), ISBN: 9781405139977, 9780470697733, p. 76-77.*
"Acetone" Internet Article from nist.gov, 5 pages.*
Gupta. Ch. 8 in Plant Pathology (2004), ISBN: 8171417892, 9788171417896, p. 276-312.*
Benedict et al. Effect of Various Factors on the Production of Polymyxin. Annals of the New York Academy of Sciences (1949), v51, p. 866-874.*
Orwa et al. Isolation and structural characterixzation opf polymyxin B components. Journal of Chromatography A (2001), v912, p. 369-373.*
Paik et al. Larvicidal toxins from *Bacillus thuringiensis* subspp. *kurstaki, morrisoni* (strain tenebrionis), and israelensis have no microbicidal or microbiostatic activity against selected bacteria, fungi, and algae in vitro. Journal of Industrial Microbiology (1997), v19, p. 294-298.*
Koskella et al. Identification and partial characterization of tochicin, a bacteriocin produced by *Bacillus thuringiensis* subsp *tochigiensis*. Canadian Journal of Microbiology (2002), v48, p. 262-267.*

(Continued)

*Primary Examiner* — Sean C. Barron
(74) *Attorney, Agent, or Firm* — Birch, Stewart, Kolasch & Birch, LLP

(57) ABSTRACT

The disclosure provides a method for manufacturing an active substance for inducing self-lysis in microalga cells, including: inoculating a bacterial strain belonging to *Bacillus* into a culturing medium to obtain a bacterial suspension; culturing the bacterial strain belonging to *Bacillus* at least to a stationary phase to a condition in which the bacterial strain belonging to *Bacillus* aggregates in the bacterial suspension and the bacterial suspension becomes pellucid; and after the bacterial strain belonging to *Bacillus* aggregates in the bacterial suspension and the bacterial suspension becomes pellucid, performing a vacuum distillation procedure on the bacterial suspension to obtain an active solution, wherein the active solution contains an active substance for inducing self-lysis in microalga cells.

24 Claims, 12 Drawing Sheets

(56) References Cited

OTHER PUBLICATIONS

Bai et al. Enhancing the oil extraction efficiency of Chlorella vulgaris with cell-disruptive pretreatment using active extracellular substances from Bacillus thuringiensis ITRI-G1. Biochemical Engineering Journal (2015), v101, p. 185-190. (Year: 2015).*
J.T. Greenplate. Quantification of Bacillus thuringiensis Insect Control Protein Cry1Ac Over Time in Bollgard Cotton Fruit and Terminals. Journal of Economic Entomology (1999), v93(6), p. 1377-1383. (Year: 1999).*
Hernandez et al. Lyophilization of lepidopteran midguts: a preserving method for Bacillus thuringiensis toxin binding studies. Journal of Invertebrate Pathology (2004), v85, p. 182-187. (Year: 2004).*
Martinez-Blanch et al. Evaluation of a Real-Time PCR Assay for the Detection and Quantification of Bacillus cereus Group Spores in Food. Journal of Food Protection (2010), v73(8), p. 1480-1485. (Year: 2010).*
Tabatabaee et al. Vacuum distillation residue upgrading by an indigenous bacillus cereus. Journal of Environmental Health Sciences & Engineering (2013), 18:11, 7 pages. (Year: 2013).*
Halim et al., "Mechanical cell disruption for lipid extraction from microalgae biomass", Bioresource Technology 140, 2013, 53-63.
Jeong et al., "Bacillamide, a novel algicide from the marine bacterium, *Bacillus* sp. SY-1, against the harmful dinoflagellate, Cochlodinium polykrikoides", Tetrahedron Letters 44, 2003, 8005-8007.
Lü et al., "Bacterial bioaugmentation for improving methane and hydrogen production from microalgae", Biotechnology for Biofuels 2013, 6:92, 1-11.
McMillan et al., "Evaluation and comparison of algal cell disruption methods: Microwave, waterbath, blender, ultrasonic and laser treatment", Applied Energy 103, 2013, 128-134.
Samek et al., "Enzymatic and Mechanical Disruption Method of Algal Cellulotic Cell Walls as a Factor Influencing Their In Vitro Digestibility", Potravinarstvo, vol. 7, Special Issue, Mar. 2013, 214-217.
Huang et al., "Identification of an Algicidal Bacteria MS7 and Primary Study on its Algicidal Activity", Oceanologia et Limnologia Sinica, vol. 44, No. 3, May 2013, pp. 632-637, with an English abstract.
Lu et al., "Isolation and Fermentation Optimization of an Ascophyllum Nodosum Degrading Strain", Journal of Shandong Agricultural University (Natural Science Edition), vol. 45, No. 4, 2014, pp. 515-521, with an English abstract.
Taiwanese Office Action and Search Report, dated Aug. 27, 2015, for Taiwanese Application No. 103144255.

* cited by examiner

METHOD FOR MANUFACTURING AN ACTIVE SUBSTANCE FOR INDUCING SELF-LYSIS IN MICROALGA CELLS, ACTIVE SUBSTANCE OBTAINED THEREFROM, AND METHOD FOR INDUCING SELF-LYSIS IN MICROALGA CELLS

CROSS REFERENCE TO RELATED APPLICATION

The present application is based on, and claims priority from, Taiwan Application Serial Number 103144255, filed on Dec. 18, 2014, the disclosure of which is hereby incorporated by reference herein in its entirety.

TECHNICAL FIELD

The technical field relates to a method for manufacturing an active substance for inducing self-lysis in microalga cells, an active substance obtained therefrom, and a method for inducing self-lysis in microalga cells.

BACKGROUND

In order to solve the problems of the greenhouse effect and rising oil prices due to the overuse of fossil fuels, a manner for transforming biomass into energy is one means of replacing traditional fossil fuels. In the development of biomass energy, microalga biodiesel is an interesting direction of research.

At present, microalgae are mainly used industrially in high unit price products, such as food, health care, biomedical products, etc. Although there is a very large of market for using microalgae in the biofuel industry, the unit price for the product is low and thus the production costs and energy consumption are aggravated. In addition, extracting oil from microalgae to form a biofuel has to disrupt cell walls of microalgae, however, this procedure is usually quite energy consuming, and thus results in the costs increasing.

In past research, it was discovered that disrupting the cell walls of microalgae using traditional methods of mechanical force consumes about 30% of the total energy contained in the microalgae, and that becomes an obstruction for industrializing microalga biofuel. Furthermore, since chemical methods for cell wall disruption need to use chemical reagents, when cells are disrupted, chemical reagents can also damage the products in the cells, and that is unfavorable to the following retrieval and use of the products. In addition, chemical disruption of cell walls also requires additional stirring power and thus makes the costs increase.

Using the traditional mechanical technique for the disruption of cell walls to treat microalgae which are high water content biomass, is highly energy consuming and does not conform with the requirements of the biofuel industry, and chemical disruption of cell walls may easily result in damage to the products in the cells, as well as requiring additional stirring power. A novel technique for the disruption of microalga cell walls that consumes less energy and costs less is needed if microalga biomass energy is to be industrialized.

SUMMARY

The disclosure provides a method for manufacturing an active substance for inducing self-lysis in microalga cells, comprising: inoculating a bacterial strain belonging to *Bacillus* into a culturing medium to obtain a bacterial suspension; culturing the bacterial strain belonging to *Bacillus* at least to a stationary phase to a condition in which the bacterial strain belonging to *Bacillus* aggregates in the bacterial suspension and the bacterial suspension becomes pellucid; and after the bacterial strain belonging to *Bacillus* aggregates in the bacterial suspension and the bacterial suspension becomes pellucid, performing a vacuum distillation procedure on the bacterial suspension to obtain an active solution, wherein the active solution contains an active substance for inducing self-lysis in microalga cells.

The disclosure further provides another method for inducing self-lysis in microalga cells, comprising: inoculating a bacterial strain belonging to *Bacillus* into a culturing medium to obtain a bacterial suspension; culturing the bacterial strain belonging to *Bacillus* at least to a stationary phase; after the bacterial strain belonging to *Bacillus* aggregates in the bacterial suspension and the bacterial suspension becomes pellucid, taking the bacterial suspension; performing a vacuum distillation procedure on the bacterial suspension which is taken to obtain an active solution, wherein the active solution contains an active substance for inducing self-lysis in microalga cells; mixing microalga cells with the active solution to form a mixture solution; and letting the mixture solution stand to make the microalga cells self-lyse and precipitate.

A detailed description is given in the following embodiments with reference to the accompanying drawings.

BRIEF DESCRIPTION OF DRAWINGS

The present invention can be more fully understood by reading the subsequent detailed description and examples with references made to the accompanying drawings, wherein.

DETAILED DESCRIPTION

Figure 1:
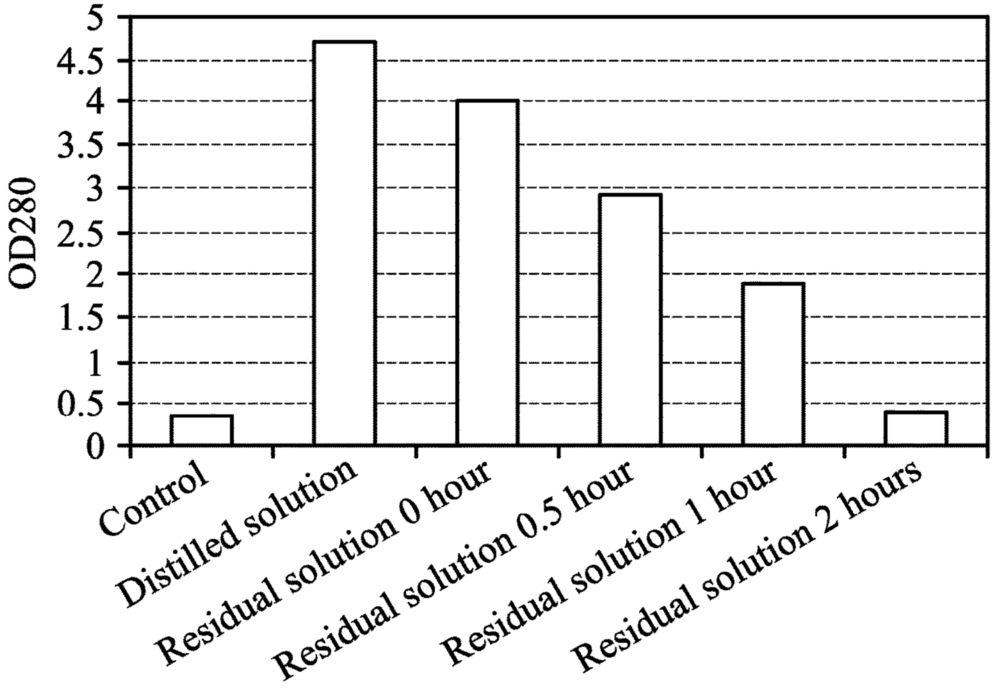
FIG. 1 shows cell disruption activities of the residual solution and the distilled solution, from the cultured medium of *Bacillus thuringiensis* ITRI-G1.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

In one embodiment, the present disclosure provides a method for manufacturing an active substance for inducing self-lysis in microalga cells. The active substance for inducing self-lysis in microalga cells of the present disclosure has the effect of inducing a series of biochemical reactions in microalga cells to make the microalga cells self-lyse.

The microalga cells mentioned herein may be unicellular algae microorganisms having cell wall shells for protection. In one embodiment, examples for the microalga cells may comprise, but are not limited to *Chlorella* sp., *Micractinium* sp., *Nannochloropsis* sp., *Tetraselmis* sp., *Isochrysis galbana, Dunaliella* sp., etc.

The method for manufacturing an active substance for inducing self-lysis in microalga cells of the present disclosure may comprise the following steps, but is not limited thereto.

First, a bacterial strain belonging to *Bacillus* is inoculated into a culturing medium to obtain a bacterial suspension.

Examples for the bacterial strain belonging to *Bacillus* mentioned above may comprise *Bacillus thuringiensis* etc., but are not limited thereto. The *Bacillus thuringiensis* mentioned above may be *Bacillus thuringiensis* BCRC 14683 (which is able to be purchased from Bioresource Collection and Research Center (BCRC), Taiwan), or *Bacillus thuringiensis* ITRI-G1 deposited in the German Collection of Microorganisms and Cell Cultures (DSMZ) on Dec. 11, 2014, under Accession number DSM 29807. In one embodiment, the bacterial strain belonging to *Bacillus* used in the method for manufacturing an active substance for inducing self-lysis in microalga cells of the present disclosure may be *Bacillus thuringiensis* ITRI-G1 deposited in the German Collection of Microorganisms and Cell Cultures (DSMZ) on Dec. 11, 2014, under Accession number DSM 29807.

In addition, there is no specific limitation for the composition of the culturing medium. In one embodiment, the composition of the foregoing culturing medium may comprise peptone, yeast extract, etc., but is not limited thereto. The concentration of the peptone in the culturing medium may be about 1-5 g/L, and the concentration of the yeast extract in the culturing medium may be about 0.1-0.5 g/L, but are not limited thereto. In one specific embodiment, the composition of the culturing medium may comprise 2 g/L peptone and 0.2 g/L yeast extract.

Then, the bacterial strain belonging to *Bacillus* in the bacterial suspension is cultured at least to a stationary phase to a condition in which the bacterial strain belonging to *Bacillus* aggregates in the bacterial suspension and the bacterial suspension becomes pellucid. In one embodiment, culturing the bacterial strain belonging to *Bacillus* in the bacterial suspension for 2-3 days may make the bacterial strain belonging to *Bacillus* aggregate in the bacterial suspension and the bacterial suspension become pellucid. In one specific embodiment, culturing the bacterial strain belonging to *Bacillus* in the bacterial suspension for 2 days may make the bacterial strain belonging to *Bacillus* aggregate in the bacterial suspension and make the bacterial suspension become pellucid.

Furthermore, the temperature for culturing the preceding bacterial strain belonging to *Bacillus* is about 20-40° C., but is not limited thereto. In one embodiment, the preceding bacterial strain belonging to *Bacillus* is cultured at 28° C.

Next, after the bacterial strain belonging to *Bacillus* aggregates in the bacterial suspension and the bacterial suspension becomes pellucid, a vacuum distillation procedure is performed on the bacterial suspension to obtain an active solution, and the active solution contains an active substance for inducing self-lysis in microalga cells.

The distillation temperature in the vacuum distillation procedure mentioned above may be about 40-90° C., but is not limited thereto. In one embodiment, the distillation temperature in the vacuum distillation procedure mentioned above may be about 40° C., about 50° C. , about 60° C., about 75° C. or about 90° C. In one specific embodiment, the distillation temperature in the vacuum distillation procedure mentioned above may be about 50° C. Moreover, the pressure in the vacuum distillation procedure mentioned above may be about 65-550 hPa, but is not limited thereto. In one embodiment, the pressure in the vacuum distillation procedure mentioned above may be about 80 hPa, about 110 hPa, about 210 hPa, about 295 hPa or about 490 hPa. In one specific embodiment, the pressure in the vacuum distillation procedure mentioned above may be about 110 hPa.

In one embodiment, the distillation temperature in the vacuum distillation procedure mentioned above may be about 40-90° C., and the pressure in the vacuum distillation procedure mentioned above may be about 65-550 hPa. In another embodiment, the distillation temperature in the vacuum distillation procedure mentioned above may be about 40° C. and the pressure in the vacuum distillation procedure mentioned above may be about 65-95 hPa, or the distillation temperature in the vacuum distillation procedure mentioned above may be about 50° C. and the pressure in the vacuum distillation procedure mentioned above may be about 105-155 hPa, or the distillation temperature in the vacuum distillation procedure mentioned above may be about 60° C. and the pressure in the vacuum distillation procedure mentioned above may be about 175-245 hPa, or the distillation temperature in the vacuum distillation procedure mentioned above may be about 75° C. and the pressure in the vacuum distillation procedure mentioned above may be about 245-345 hPa, or the distillation temperature in the vacuum distillation procedure mentioned above may be about 90° C. and the pressure in the vacuum distillation procedure mentioned above may be about 430-550 hPa. Moreover, in one specific embodiment, the distillation temperature in the vacuum distillation procedure mentioned above may be about 50° C. and the pressure in the vacuum distillation procedure mentioned above may be about 110 hPa.

In one embodiment, the method for manufacturing an active substance for inducing self-lysis in microalga cells of the present disclosure mentioned above may further comprise a step of isolating the active substance for inducing self-lysis in microalga cells from the active solution through high-performance liquid chromatography.

In another embodiment, the method for manufacturing an active substance for inducing self-lysis in microalga cells of the present disclosure mentioned above may further comprise a step of heating the obtained active solution to prevent the active substance for inducing self-lysis in microalga cells therein to aggregate and decrease activity. The temperature for heating the active solution may be about 50-90° C., and in one embodiment, the temperature for heating the active solution is about 60° C. Furthermore, time for heating the active solution may be about 2-10 hours, and in one embodiment, a heating time for the active solution is about 8 hours. In one embodiment, the temperature for heating the active solution may be about 60-80° C., and the time required to heat the active solution may be about 6-8 hours. In one specific embodiment, the temperature for heating the active solution may be about 60, 70 or 80° C., and the time required to heat the active solution may be about 8 hours.

In another embodiment, the present disclosure also provides an active substance for inducing self-lysis in microalga cells. The active substance for inducing self-lysis in microalga cells of the present disclosure may be obtained by any one of the methods for manufacturing an active substance for inducing self-lysis in microalga cells of the present disclosure mentioned above.

In another embodiment, the present disclosure further provides a method for inducing self-lysis in microalga cells. The method for inducing self-lysis in microalga cells of the present disclosure mentioned herein may comprise the following steps, but is not limited thereto.

First, microalga cells are put in contact with the active substance for inducing self-lysis in microalga cells obtained by any one of the methods for manufacturing an active substance for inducing self-lysis in microalga cells of the present disclosure mentioned above, to induce self-lysis in the microalga cells.

The microalga cells mentioned herein may be unicellular algae microorganisms having cell wall shells for protection, such as *Chlorella* sp., *Micractinium* sp., *Nannochloropsis* sp., *Tetraselmis* sp., *Isochrysis galbana, Dunaliella* sp., etc. In one embodiment, the microalga cells are microalga cells in a condition of being fresh and alive.

The step of contacting the microalga cells with the active substance for inducing self-lysis in microalga cells of the present disclosure does not have any specific limitation while only needs to make the microalga cells contact with the active substance for inducing self-lysis in microalga cells, for example, the active substance for inducing self-lysis in microalga cells itself can be added to a solution containing the microalga cells, or the microalga cells can be mixed with an active solution containing the active substance for inducing self-lysis in microalga cells.

In one embodiment, the step of contacting the microalga cells with the active substance for inducing self-lysis in microalga cells of the present disclosure may comprise, but is not limited to, mixing the microalga cells with the active solution to form a mixture solution, and after that letting the mixture solution stand, or continuously stirring the mixture solution and then letting it stand, to make the microalga cells self-lyse and precipitate. In addition, the microalga cells may account for about 4-50 wt % of the preceding mixture solution, such as 10 wt %.

Since the active substance for inducing self-lysis in microalga cells of the present disclosure has the effect of inducing a series of biochemical reactions in microalga cells to make the microalga cells self-lyse and cell lysis is due to intracellular biochemical reactions, the method for inducing self-lysis in microalga cells has low demand on mass transportation through stirring, and can be performed under a low stirring conditions or even without stirring.

In one embodiment, the step of contacting the microalga cells with the active substance for inducing self-lysis in microalga cells of the present disclosure may comprise, but is not limited to, mixing the microalga cells with the active solution to form a mixture solution, and after that letting the mixture solution stand to make the microalga cells self-lyse and precipitate. In this embodiment, the mixture solution may be left to stand for about 5-30 hours, such as about 8, 12 and 24 hours. Furthermore, there is no specific limitation on the temperature for letting the mixture solution stand. In one embodiment, the mixture solution may be left to stand at a room temperature.

In one embodiment, the foregoing method for inducing self-lysis in microalga cells of the present disclosure may further comprise before contacting the microalga cells with the active substance for inducing self-lysis in microalga cells obtained by any one of the methods for manufacturing an active substance for inducing self-lysis in microalga cells of the present disclosure mentioned above, previously heating the active solution containing the active substance for inducing self-lysis in microalga cells to prevent the active substance for inducing self-lysis in microalga cells therein to aggregate and decrease activity. The temperature for heating the active solution containing the active substance for inducing self-lysis in microalga cells may be about 50-90° C. , such as 60° C., but is not limited thereto. Furthermore, the time required to heat the active solution containing the active substance for inducing self-lysis in microalga cells may be about 2-10 hours, such as 8 hours, but is not limited thereto. In one embodiment, the temperature for heating the active solution is about 60-80° C., and the time required to heat the active solution is about 6-8 hours. In one specific embodiment, the temperature for heating the active solution is about 60, 70 or 80° C., and the time required to heat the active solution is about 8 hours.

In another embodiment, the foregoing method for inducing self-lysis in microalga cells of the present disclosure may further comprise after the microalga cells precipitate, retrieving a supernatant of the mixture solution to retrieve the active substance for inducing self-lysis in microalga cells in the supernatant.

In this embodiment, the foregoing method for inducing self-lysis in microalga cells of the present disclosure also may further comprise a step of heating the supernatant to prevent the active substance for inducing self-lysis in microalga cells therein to aggregate and decrease activity. The temperature for heating the supernatant which is retrieved may be about 50-90° C., such as 60° C., but is not limited thereto. Furthermore, the time required to heat the supernatant which is retrieved may be about 2-10 hours, such as 8 hours, but is not limited thereto. In one embodiment, the temperature for heating the supernatant which is retrieved is about 60-80° C., and the time required to heat the supernatant which is retrieved is about 6-8 hours. In one specific embodiment, the temperature for heating the supernatant which is retrieved is about 60, 70 or 80° C., and the time required to heat the supernatant which is retrieved is about 8 hours.

In another embodiment, the present disclosure provides another method for inducing self-lysis in microalga cells. The method for inducing self-lysis in microalga cells of the present disclosure mentioned herein may comprise the following steps, but is not limited thereto.

First, a bacterial strain belonging to *Bacillus* is inoculated into a culturing medium to obtain a bacterial suspension.

A bacterial strain belonging to *Bacillus* which is suitable for use in the method for inducing self-lysis in microalga cells of the present disclosure mentioned herein may comprise, but is not limited to *Bacillus thuringiensis*. Examples for the *Bacillus thuringiensis* mentioned above may be *Bacillus thuringiensis* BCRC 14683 (which is able to be purchased from Bioresource Collection and Research Center (BCRC), Taiwan), and *Bacillus thuringiensis* ITRI-G1 deposited in the German Collection of Microorganisms and Cell Cultures (DSMZ) on Dec. 11, 2014, under Accession number DSM 29807, etc., but are not limited thereto. In one embodiment, the bacterial strain belonging to *Bacillus* used in the method for inducing self-lysis in microalga cells of the present disclosure mentioned herein may be *Bacillus thuringiensis* ITRI-G1 deposited in the German Collection of Microorganisms and Cell Cultures (DSMZ) on Dec. 11, 2014, under Accession number DSM 29807.

In addition, there is no specific limitation for the composition of a culturing medium which is suitable for use in the method for inducing self-lysis in microalga cells of the present disclosure mentioned herein. In one embodiment, the culturing medium which is suitable for use in the method for inducing self-lysis in microalga cells of the present disclosure mentioned herein is a culturing medium suitable for growth of a bacterial strain belonging to *Bacillus*. In another embodiment, the composition of the culturing medium may comprise peptone, yeast extract, etc., but is not limited thereto. The concentration of the peptone mentioned above in the culturing medium may be about 1-5 g/L, and the concentration of the yeast extract mentioned above in the culturing medium may be about 0.1-0.5 g/L, but they are not limited thereto. In one specific embodiment, the composition of the culturing medium may comprise 2 g/L peptone and 0.2 g/L yeast extract.

Then, the bacterial strain belonging to *Bacillus* in the bacterial suspension is at least to a stationary phase to a condition in which the bacterial strain belonging to *Bacillus* aggregates in the bacterial suspension and the bacterial suspension becomes pellucid. In one embodiment, culturing the bacterial strain belonging to *Bacillus* in the bacterial suspension for 2-3 days may make the bacterial strain belonging to *Bacillus* aggregate in the bacterial suspension and the bacterial suspension become pellucid. In one specific embodiment, culturing the bacterial strain belonging to *Bacillus* in the bacterial suspension for 2 days may make the bacterial strain belonging to *Bacillus* aggregate in the bacterial suspension and the bacterial suspension become pellucid. In addition, the temperature for culturing the bacterial strain belonging to *Bacillus* is about 20-40° C., such as 28° C., but is not limited thereto.

Afterward, after the bacterial strain belonging to *Bacillus* aggregates in the bacterial suspension and the bacterial suspension becomes pellucid, a vacuum distillation procedure is performed on the bacterial suspension to obtain an active solution, and the active solution contains an active substance for inducing self-lysis in microalga cells.

A temperature and a pressure which are suitable to be adopted by the vacuum distillation procedure for the active solution are described below. The distillation temperature in the vacuum distillation procedure mentioned above may be about 40-90° C., such as 40° C., about 50° C., about 60° C., about 75° C., about 90° C., etc., but is not limited thereto, and in one specific embodiment, the distillation temperature in the vacuum distillation procedure mentioned above may be about 50° C. . Furthermore, the pressure in the vacuum distillation procedure mentioned above may be about 65-550 hPa, for example, in one embodiment, the pressure in the vacuum distillation procedure mentioned above may be about 80 hPa, about 110 hPa, about 210 hPa, about 295 hPa or about 490 hPa. In one specific embodiment, the pressure in the vacuum distillation procedure mentioned above may be about 110 hPa.

In one embodiment, the distillation temperature in the vacuum distillation procedure mentioned above may be about 40-90 ° C. , and the pressure in the vacuum distillation procedure mentioned above may be about 65-550 hPa. In another embodiment, the distillation temperature in the vacuum distillation procedure mentioned above may be about 40° C. and the pressure in the vacuum distillation procedure mentioned above may be about 65-95 hPa, or the distillation temperature in the vacuum distillation procedure mentioned above may be about 50° C. and the pressure in the vacuum distillation procedure mentioned above may be about 105-155 hPa, or the distillation temperature in the vacuum distillation procedure mentioned above may be about 60° C. and the pressure in the vacuum distillation procedure mentioned above may be about 175-245 hPa, or the distillation temperature in the vacuum distillation procedure mentioned above may be about 75° C. and the pressure in the vacuum distillation procedure mentioned above may be about 245-345 hPa, or the distillation temperature in the vacuum distillation procedure mentioned above may be about 90° C. and the pressure in the vacuum distillation procedure mentioned above may be about 430-550 hPa. Furthermore, in one specific embodiment, the distillation temperature in the vacuum distillation procedure mentioned above may be about 50° C. and the pressure in the vacuum distillation procedure mentioned above may be about 110 hPa.

Next, microalga cells are mixed with the active solution containing the active substance for inducing self-lysis in microalga cells to form a mixture solution. The microalga cells may account for about 4-50 wt % of the preceding mixture solution, such as 10 wt %. The microalga cells mentioned herein may be unicellular algae microorganisms having cell wall shells for protection, such as *Chlorella* sp., *Nannochloropsis* sp., *Tetraselmis* sp., *Isochrysis galbana, Dunaliella* sp., etc. In one embodiment, the microalga cells are microalga cells in a condition of being fresh and alive.

Finally, the mixture solution is left to stand to make the microalga cells self-lyse and precipitate. The preceding mixture solution may be left to stand for about 5-30 hours, such as about 8, 12 and 24 hours. In one embodiment, the preceding mixture solution is left to stand for about 8-24 hours. In one specific embodiment, the preceding mixture solution is left to stand for about 8, 12 or 24 hours. In addition, there is no specific limitation on the temperature for letting the mixture solution stand. In one embodiment, the mixture solution may be left to stand at a room temperature.

Moreover, in one embodiment, the method for inducing self-lysis in microalga cells of the present disclosure mentioned herein may further comprise a step of isolating the active substance for inducing self-lysis in microalga cells from the obtained active solution through high-performance liquid chromatography before mixing microalga cells with the foregoing active solution.

Furthermore, in one embodiment, the method for inducing self-lysis in microalga cells of the present disclosure mentioned herein may further comprise before mixing microalga cells with the foregoing active solution, heating the obtained active solution to prevent the active substance for inducing self-lysis in microalga cells therein to aggregate and decrease activity.

The temperature for heating the active solution containing the active substance for inducing self-lysis in microalga cells may be about 50-90° C., such as 60° C., but is not limited thereto. In addition, the time required to heat the active solution containing the active substance for inducing self-lysis in microalga cells may be about 2-10 hours, such as 8 hours, but is not limited thereto. In one embodiment, the temperature for heating the active solution is about 60-80° C., and the time required to heat the active solution is about 6-8 hours. In one specific embodiment, the temperature for heating the active solution is about 60, 70 or 80° C., and the time required to heat the active solution is about 8 hours.

Moreover, in another embodiment, the method for inducing self-lysis in microalga cells of the present disclosure mentioned herein may further comprise after the microalga cells precipitate, retrieving a supernatant of the mixture solution to retrieve the active substance for inducing self-lysis in microalga cells in the supernatant.

In this embodiment, the method for inducing self-lysis in microalga cells of the present disclosure mentioned herein also may further comprise a step of heating the supernatant to prevent the active substance for inducing self-lysis in microalga cells therein to aggregate and decrease activity. The temperature for heating the supernatant which is retrieved may be about 50-90° C., such as 60° C., but is not limited thereto. Furthermore, the time required to heat the supernatant which is retrieved may be about 2-10 hours, such as 8 hours, but is not limited thereto. In one embodiment, the temperature for heating the supernatant which is retrieved is about 60-80° C., and the time required to heat the supernatant which is retrieved is about 6-8 hours. In one specific embodiment, the temperature for heating the supernatant which is retrieved is about 60, 70 or 80° C., and the time required to heat the supernatant which is retrieved is about 8 hours.

Through the method for inducing self-lysis in microalga cells of the present disclosure, disruption of microalga cells can be accomplished only by mixing microalga cells with the active solution containing the active substance for inducing self-lysis in microalga cells and then letting the formed mixture solution stand without stirring and/or other treatment.

In addition, after the disruption of microalga cells is completed, the active substance for inducing self-lysis in microalga cells used in the method for inducing self-lysis in microalga cells of the present disclosure also can be easily retrieved and newly used. Accordingly, it is known that the method for inducing self-lysis in microalga cells of the present disclosure has the advantages of being easy to operate, saving energy resources, reducing costs, etc. and is a novel microalgae cell disruption method which consumes little power, costs little, and uses recyclable materials.

EXAMPLES

Example 1

Determination for volatility of the active substance for inducing self-lysis in microalga cells 1. Treatment for cultured medium of *Bacillus thuringiensis* ITRI-G1 (which was deposited in the German Collection of Microorganisms and Cell Cultures (DSMZ) on Dec. 11, 2014, under Accession number DSM 29807)

(1) Culture of *Bacillus thuringiensis* ITRI-G1

*Bacillus thuringiensis* ITRI-G1 was cultured by the culturing medium and culturing conditions shown below.

Culturing medium: 2 g/L peptone+0.2 g/L yeast extract

Culturing conditions: Under a shaking rate of 150 rpm, culturing at 28° C. for 2 days After culture of *Bacillus thuringiensis* ITRI-G1 was completed, 300 mL cultured medium was taken and a vacuum distillation procedure was performed thereon. Under different distillation time periods, a residual solution (non-volatilized part) was collected, and when the vacuum distillation procedure was performed for 2 hours, a whole distilled solution was collected. Conditions for the vacuum distillation procedure are shown below.

Distillation temperature: 50° C.

Pressure: 110 hPa

Time: 2 hours

2. Disruption Test for *Chlorella* sp.

Fresh *Chlorella* sp. was prepared to a *Chlorella* sp. suspension with a concentration of about 150 g/L. Then, the residual solution or distilled solution was added to the *Chlorella* sp. suspension to a concentration of *Chlorella* sp. suspension of 10 g/L.

After that, the optical absorbance of the *Chlorella* sp. suspension was measured at 280 nm to estimate the amount of protein which is released from *Chlorella* sp. due to disruption of cell walls. The results are shown in FIG. 1.

According to FIG. 1, it is clearly known that with the distillation time increasing, the cell disruption activity of the residual solution progressively decreased. After being distilled for 2 hours, the residual solution almost had no cell disruption activity. On the contrary, the distilled solution showed a quite high cell disruption activity.

Therefore, according to the foregoing, it is understood that the active substance for inducing self-lysis in microalga cells produced by *Bacillus thuringiensis* ITRI-G1 was completely evaporated and the active substance for inducing self-lysis in microalga cells produced by *Bacillus thuringiensis* ITRI-G1 exists in the distilled solution.

Example 2

Disruption test for *Chlorella* sp. through an active substance for inducing self-lysis in microalga cells 1. Preparation of the Active Substance for Inducing Self-Lysis in Microalga Cells (1) Culture of *Bacillus thuringiensis* ITRI-G1

*Bacillus thuringiensis* ITRI-G1 was cultured by the culturing medium and culturing conditions shown below.

Culturing medium: 2 g/L peptone+0.2 g/L yeast extract

Culturing conditions: Under a shaking rate of 150 rpm, culturing at 28° C. for 2 days (2) Isolation and Purification for the Active Substance for Inducing Self-lysis in Microalga Cells After culture of *Bacillus thuringiensis* ITRI-G1 was completed, 300 mL cultured medium was taken, isolated and purified through a vacuum distillation procedure, and then 100 mL distilled solution was obtained. Conditions for the vacuum distillation procedure are shown below.

Distillation temperature: 50° C.

Pressure: 110 hPa

Time: 2 hours

2. Disruption of *Chlorella* sp.

Fresh *Chlorella* sp. was prepared to a *Chlorella* sp. suspension with a concentration of about 150 g/L. Then, the foregoing obtained distilled solution was added to the *Chlorella* sp. suspension to a concentration of *Chlorella* sp. suspension of 10 g/L.

After that, a part of the *Chlorella* sp. suspension was taken at different time point and the optical absorbance thereof was measured at 280 nm to estimate the amount of protein which is released from *Chlorella* sp. due to disruption of cell wall. The results are shown in FIG. 2, wherein Test 1 and Test 2 are repeated trials.

Figure 2:
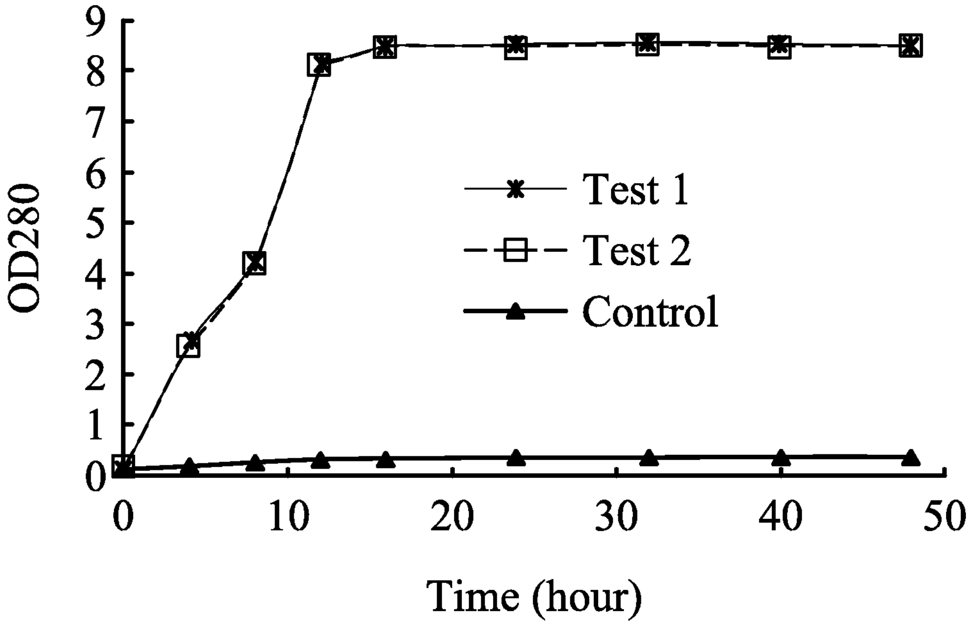
FIG. 2 shows the effect of different treatment time of the active substance for inducing self-lysis in microalga cells of the present disclosure on disruption of microalga cells.

According to FIG. 2, it is clearly known that the foregoing obtained distilled solution can make microalga cells disrupt and self-lyse indeed.

Example 3

Effects of the active substance for inducing self-lysis in microalga cells on different kinds of microalga cells 1. Preparation of the Active Substance for Inducing Self-lysis in Microalga Cells (1) Culture of *Bacillus thuringiensis* ITRI-G1 and *Bacillus thuringiensis* BCRC14683 (purchased from Bioresource Collection and Research Center (BCRC), Taiwan)

*Bacillus thuringiensis* ITRI-G1 and *Bacillus thuringiensis* BCRC14683 was cultured by the culturing medium and culturing conditions shown separately below.

Culturing medium: 2 g/L peptone+0.2 g/L yeast extract

Culturing conditions: Under a shaking rate of 150 rpm, culturing at 28° C. for 2 days (2) Isolation and Purification for the Active Substance for Inducing Self-lysis in Microalga Cells After culture of *Bacillus thuringiensis* ITRI-G1 and *Bacillus thuringiensis* BCRC14683 was completed, 300 mL cultured medium was taken, isolated and purified through a vacuum distillation procedure, and then 100 mL distilled solution was obtained. Conditions for the vacuum distillation procedure are shown below.

Distillation temperature: 50° C.

Pressure: 110 hPa

Time: 2 hours

2. Microalgae Disruption

Fresh microalgae were prepared to a microalgae suspension with a concentration of about 150 g/L. Then, the foregoing obtained distilled solution was added to the microalgae suspension (for control group, water was added to the microalgae suspension) to a concentration of microalgae suspension of 5 g/L. Next, the suspension was left to stand for 24 hours. The kinds of microalgae tested by the active substance for inducing self-lysis in microalga cells obtained by Bacillus thuringiensis ITRI-G1 comprised *Chlorella* sp., *Micractinium* sp. and *Nannochloropsis* sp., and the kinds of microalgae tested by the active substance for inducing self-lysis in microalga cells obtained by *Bacillus thuringiensis* BCRC14683 comprised *Chlorella* sp. and *Micractinium* sp.

After that, a part of the suspension was taken at different time points and the optical absorbance thereof was measured at 280 nm to estimate the amount of protein released from the microalgae due to disruption of cell wall. The effects of the active substance for inducing self-lysis in microalga cells existing in the distilled solution on *Chlorella* sp., *Micractinium* sp. and *Nannochloropsis* sp. are shown in FIGS. 3A, 3B and 3C, respectively.

Figure 3A:
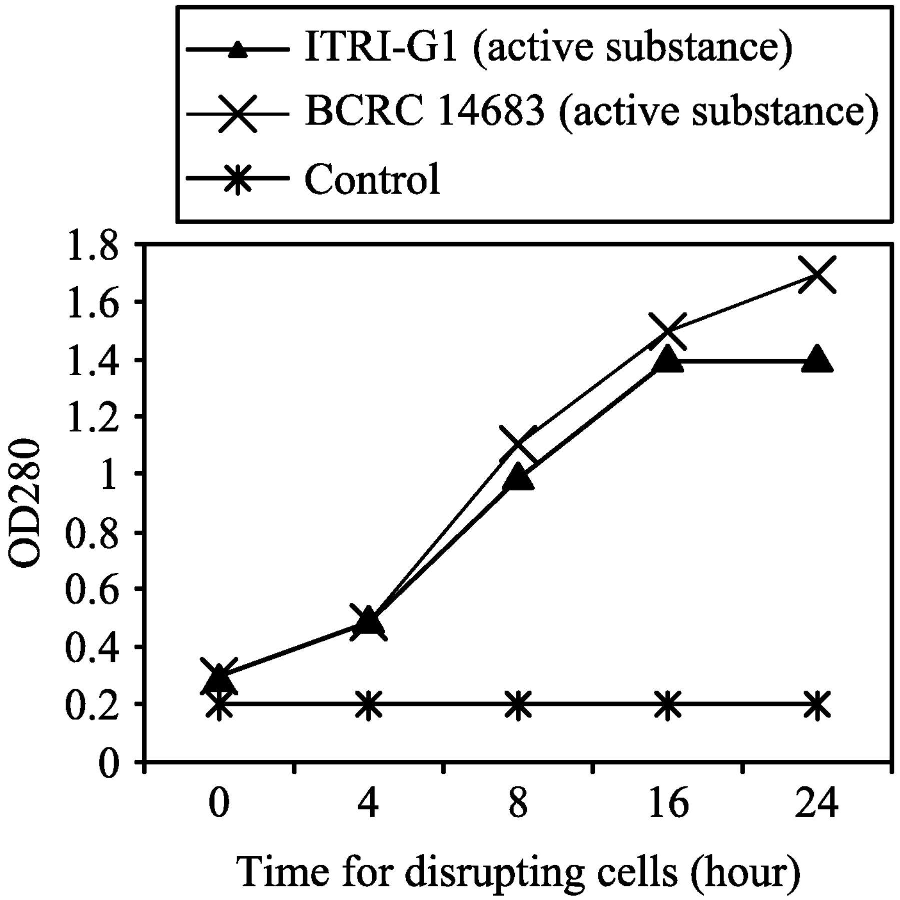
FIG. 3A shows the effect of different treatment time of the active substance for inducing self-lysis in microalga cells of the present disclosure on disruption of *Chlorella* sp.
Figure 3B:
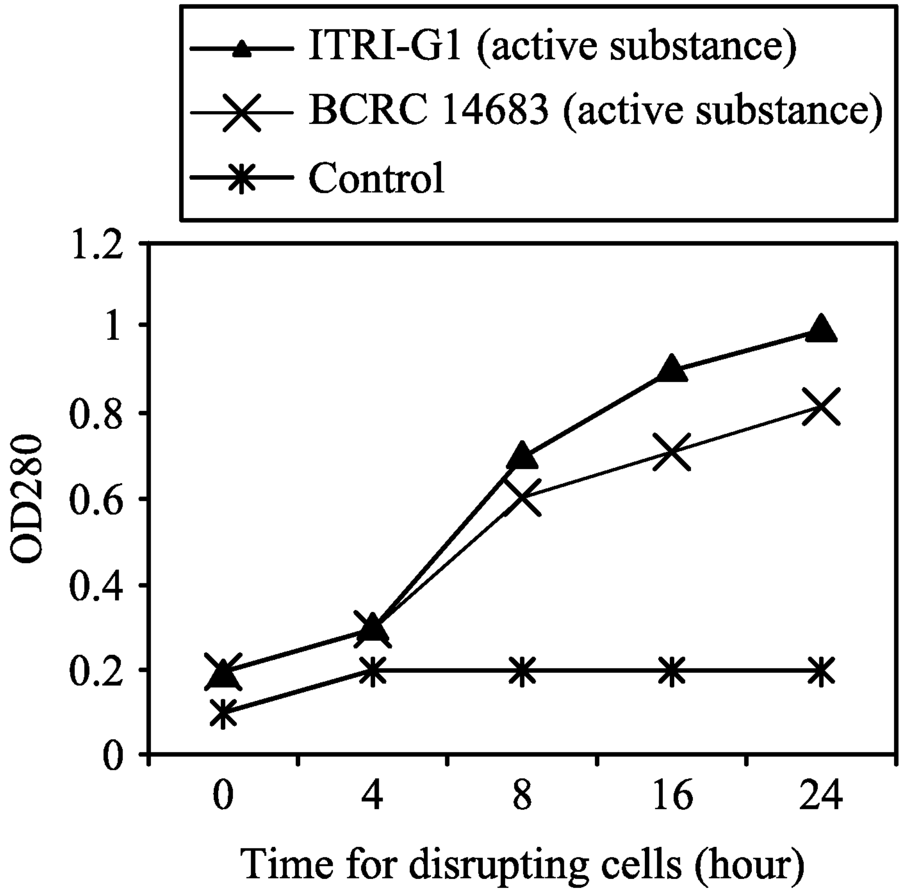
FIG. 3B shows the effect of different treatment time of the active substance for inducing self-lysis in microalga cells of the present disclosure on disruption of *Micractinium* sp.
Figure 3C:
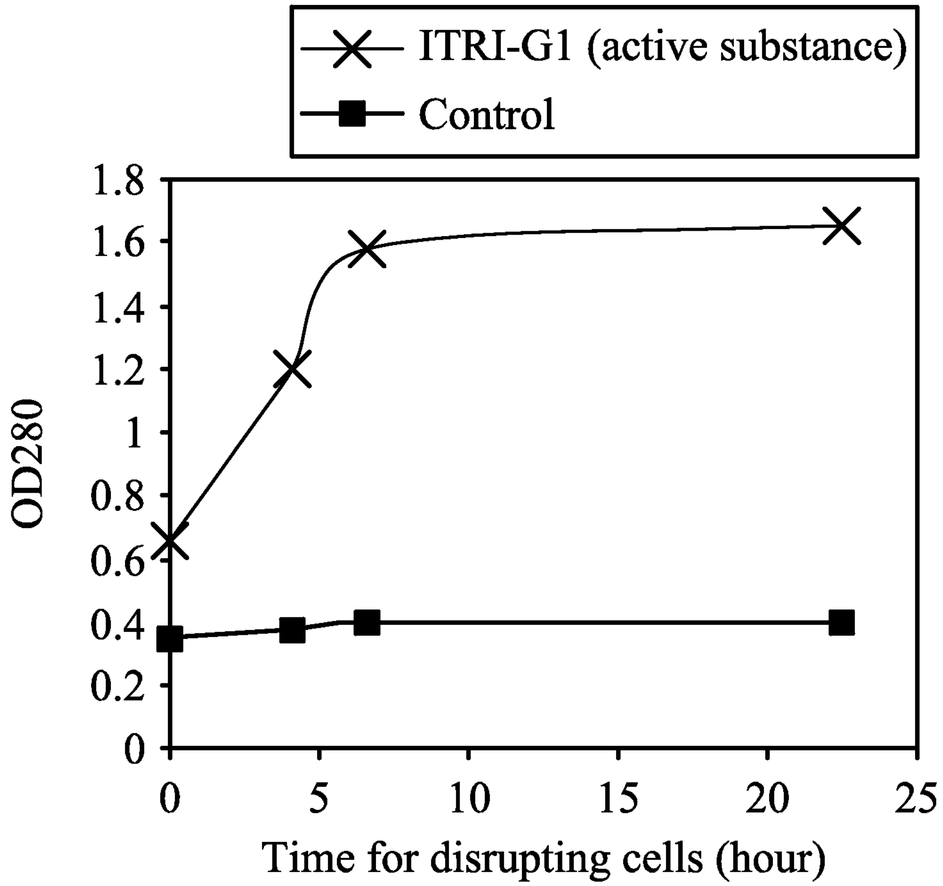
FIG. 3C shows the effect of different treatment time of the active substance for inducing self-lysis in microalga cells of the present disclosure on disruption of *Nannochloropsis* sp.

According to FIGS. 3A, 3B and 3C, it is known that the active substance for inducing self-lysis in microalga cells existing in the distilled solution has an effect on all of *Chlorella* sp., *Micractinium* sp. and *Nannochloropsis* sp.

Example 4

Effectiveness evaluation of the active substance for inducing self-lysis in microalga cells after being frozen and after being frozen and then heated 1. Preparation of the Active Substance for Inducing Self-lysis in Microalga Cells (1) Culture of *Bacillus thuringiensis* ITRI-G1

*Bacillus thuringiensis* ITRI-G1 was cultured by the culturing medium and culturing conditions shown below.

Culturing medium: 2 g/L peptone+0.2 g/L yeast extract

Culturing conditions: Under a shaking rate of 150 rpm, culturing at 28° C. for 2 days (2) Isolation and Purification for the Active Substance for Inducing Self-lysis in Microalga Cells After culture of *Bacillus thuringiensis* ITRI-G1 was completed, 300 mL cultured medium was taken, isolated and purified through a vacuum distillation procedure, and then 100 mL distilled solution was obtained. Conditions for the vacuum distillation procedure are shown below.

Distillation temperature: 50° C.

Pressure: 110 hPa

Time: 2 hours (3) Freezing and Heating After Freezing for the Active Substance for Inducing Self-Lysis in Microalga Cells The preceding distilled solution (active substance solution) was placed at −20° C. to be frozen for different time period, and then was taken to be unfrozen at a room temperature.

The distilled solution (active substance solution) which had been frozen for 72 hours was placed in a 60° C., 70° C. or 80° C. high temperature water bath for 8 hours after being unfrozen.

(4) Disruption of *Chlorella* sp.

Fresh *Chlorella* sp. was prepared to a *Chlorella* sp. suspension with a concentration of about 150 g/L. Then, the foregoing obtained frozen distilled solution or frozen and then heated distilled solution was added to the *Chlorella* sp. suspension to a concentration of *Chlorella* sp. suspension of 10 g/L.

After that, a part of the *Chlorella* sp. suspension was taken at different time point and the optical absorbance thereof was measured at 280 nm to estimate the amount of protein which is released from *Chlorella* sp. due to disruption of cell wall. Disruption effects of the frozen distilled solution and the frozen and then heated distilled solution are shown in FIGS. 4A and 4B, respectively.

Figure 4A:
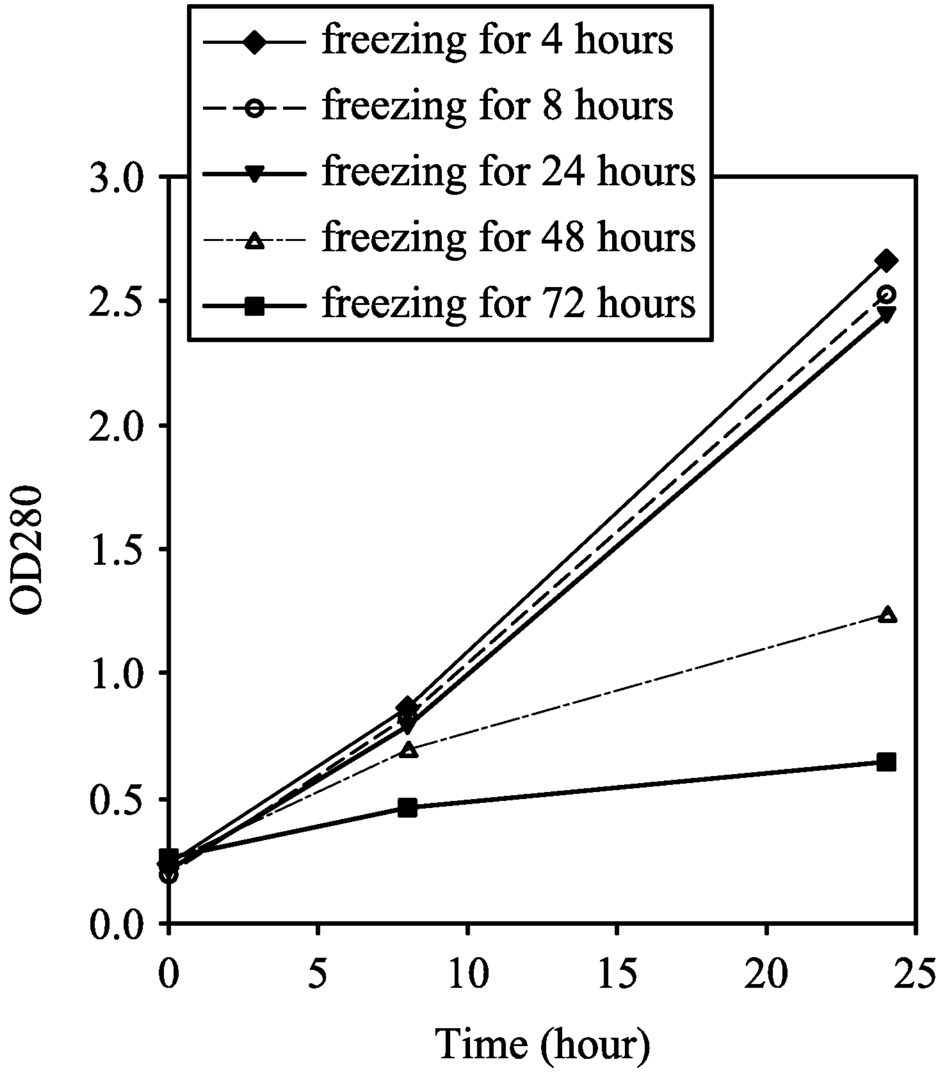
FIG. 4A shows the effect of freezing on the active substance for inducing self-lysis in microalga cells of the present disclosure.
Figure 4B:
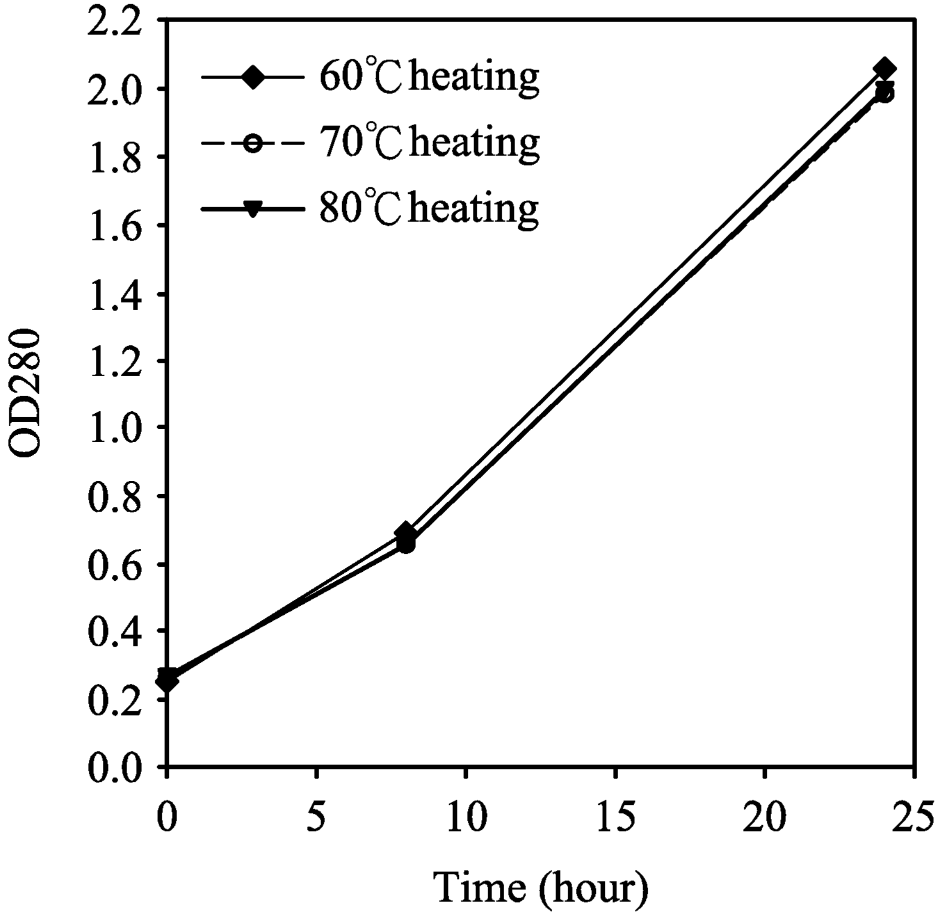
FIG. 4B shows the effect of heating on the frozen active substance for inducing self-lysis in microalga cells of the present disclosure.

According to FIGS. 4A and 4B, it is understood that with the freezing time increasing, the cell disruption activity of the distilled solution progressively decreases. After being frozen for 72 hours, the distilled solution almost had no cell disruption activity. On the contrary, when the frozen distilled solution was then heated further, the activity of the distilled solution could recover to 70% (as compared to the activity of a distilled solution which was not frozen (not shown)).

Therefore, according to the information mentioned above, it is known that freezing will make the active substance for inducing self-lysis in microalga cells existing in the distilled solution deactivate, and on the contrary, heating can recover the activity of the active substance for inducing self-lysis in microalga cells existing in the distilled solution.

Example 5

Extraction of oil in microalgae through disruption of microalgae induced by the active substance for inducing self-lysis in microalga cells 1. Preparation of the Active Substance for Inducing Self-lysis in Microalga Cells (1) Culture of *Bacillus thuringiensis* ITRI-G1

*Bacillus thuringiensis* ITRI-G1 was cultured by the culturing medium and culturing conditions shown below.

Culturing medium: 2 g/L peptone +0.2 g/L yeast extract

Culturing conditions: Under a shaking rate of 150 rpm, culturing at 28° C. for 2 days (2) Isolation and Purification for the Active Substance for Inducing Self-lysis in Microalga Cells After culture of *Bacillus thuringiensis* ITRI-G1 was completed, 300 mL cultured medium was taken, isolated and purified through a vacuum distillation procedure, and then 100 mL distilled solution was obtained. Conditions for the vacuum distillation procedure are shown below.

Distillation temperature: 50° C.

Pressure: 110 hPa

Time: 2 hours

2. Disruption of *Chlorella* sp.

Fresh *Chlorella* sp. was prepared to a *Chlorella* sp. suspension with a concentration of about 150 g/L. Then, the foregoing obtained distilled solution was added to the *Chlorella* sp. suspension to a concentration of *Chlorella* sp. suspension of 10 g/L. Then the suspension was left to stand for 24 hours.

3. Extraction for Oil in *Chlorella* sp. Cells

After the suspension was left to stand for 24 hours as mentioned above, the suspension was centrifuged to obtain *Chlorella* sp. cells. Then, oil extraction was performed on the *Chlorella* sp. cells and a fatty acid methyl ester (FAME) analysis was performed to determine the oil content.

4. Retrieval of the Active Substance for Inducing Self-lysis in Microalga Cells

After the suspension was left to stand for 24 hours as mentioned above, the suspension was centrifuged to obtain a supernatant. A vacuum distillation procedure was performed on 300 mL of the suspension and then 100 mL distilled solution was obtained. Conditions for the vacuum distillation procedure are shown below.

Distillation temperature: 50° C.

Pressure: 110 hPa

Time: 2 hours

5. Effectiveness Test for Retrieved Active Substance

Based on the microalgae disruption method mentioned above, the microalgae were disrupted by the retrieved distilled solution, and after the microalgae were disrupted, the oil content of the microalgae was determined through an analysis that was the same as that mentioned above, and the retrieved active substance was retrieved again. The retrieved active substance was repeatedly retrieved and reused, and the oil content of the microalgae after being disrupted was determined, 4 times. The results are shown in FIG. 5.

Figure 5:
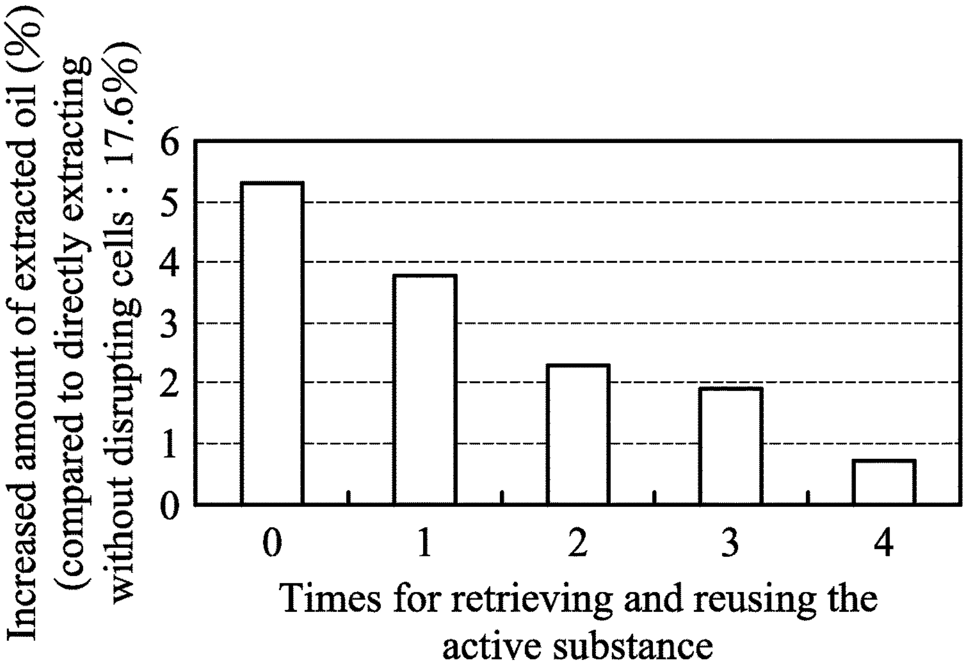
FIG. 5 shows effect of the retrieved active substance on promotion of oil extraction for microalgae.

According to FIG. 5, it is known that the active substance has effects of inducing cell disruption of microalgae and promoting extraction of oil, and the active substance after being used can be retrieved and continuously reused for cell disruption of microalgae but the activity thereof will slightly decrease.

Example 6

Effect of Stirring on Cell Disruption of Microalgae Induced by the Active Substance 1. Preparation of the active substance for inducing self-lysis in microalga cells (1) Culture of *Bacillus thuringiensis* ITRI-G1

*Bacillus thuringiensis* ITRI-G1 was cultured by the culturing medium and culturing conditions shown below.

Culturing medium: 2 g/L peptone+0.2 g/L yeast extract

Culturing conditions: Under a shaking rate of 150 rpm, culturing at 28° C. for 2 days (2) Isolation and Purification for the Active Substance for Inducing Self-lysis in Microalga Cells After culture of *Bacillus thuringiensis* ITRI-G1 was completed, 300 mL cultured medium was taken, isolated and purified through a vacuum distillation procedure, and then 100 mL distilled solution was obtained. Conditions for the vacuum distillation procedure are shown below.

Distillation temperature: 50° C.

Pressure: 110 hPa

Time: 2 hours

2. Disruption of *Chlorella* sp.

Fresh *Chlorella* sp. was prepared to a *Chlorella* sp. suspension with a concentration of about 150 g/L. Then, the foregoing obtained distilled solution was added to the *Chlorella* sp. suspension to a concentration of *Chlorella* sp. suspension of 10 g/L. Afterward, the *Chlorella* sp. suspension was left standing (without stirring) or the *Chlorella* sp. suspension was horizontally shaken at 100 rpm.

After that, a part of the *Chlorella* sp. suspension was taken at different time point and the optical absorbance thereof was measured at 280 nm to estimate the amount of protein which is released from *Chlorella* sp. due to disruption of cell wall. The results are shown in FIG. 6.

Figure 6:
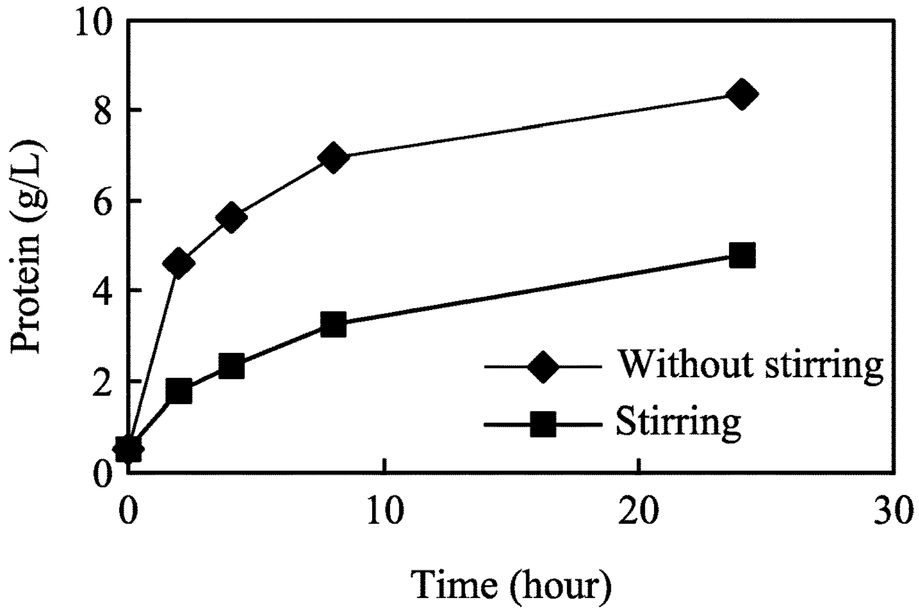
FIG. 6 shows effect of stirring on cell disruption of microalgae induced by the active substance.

According to FIG. 6, it is clearly understood that cell disruption can be completed in about 12-16 hours under conditions that did not include stirring. Moreover, as compared to the stirring treatment, the active substance has better efficiency of cell disruption of microalgae under conditions that did not include stirring. Both the initial efficiency and the final efficiency of the cell disruption of the microalgae of the active substance under conditions that did not include stirring were greater than those under conditions that included stirring at 100 rpm for about 100%.

Example 7

Effectiveness test of the Distilled Solution of the Cultured Medium Obtained from Culturing Bacteria for Different Time Period 1. Preparation of the Active Substance for Inducing Self-lysis in Microalga Cells (1) Culture of *Bacillus thuringiensis* ITRI-G1

*Bacillus thuringiensis* ITRI-G1 was cultured by the culturing medium and culturing conditions shown below.

Culturing medium: 2 g/L peptone +0.2 g/L yeast extract

Culturing conditions:

(i) Under a shaking rate of 150 rpm, culturing at 28° C. for 1 day;

(ii) Under a shaking rate of 150 rpm, culturing at 28° C. for 2 days;

(2) Vacuum Distillation Procedure

After culture of *Bacillus thuringiensis* ITRI-G1 was completed, 300 mL cultured medium was taken, isolated and purified through a vacuum distillation procedure, and then 100 mL distilled solution was obtained. Conditions for the vacuum distillation procedure are shown below.

Distillation temperature: 50° C.

Pressure: 110 hPa

Time: 2 hours

2. Disruption of *Chlorella* sp.

Fresh *Chlorella* sp. was prepared to a *Chlorella* sp. suspension with a concentration of about 150 g/L. Then, the foregoing obtained distilled solution was added to the *Chlorella* sp. suspension to a concentration of *Chlorella* sp. suspension of 10 g/L. Afterward, the *Chlorella* sp. suspension was left standing for 24 hours.

3. Extraction for Oil in *Chlorella* sp. Cells

After the suspension was left to stand for 24 hours as mentioned above, the suspension was centrifuged to obtain *Chlorella* sp. cells. Then, oil extraction was performed on the *Chlorella* sp. cells and a fatty acid methyl ester (FAME) analysis was performed to determine the oil content.

Figure 7:
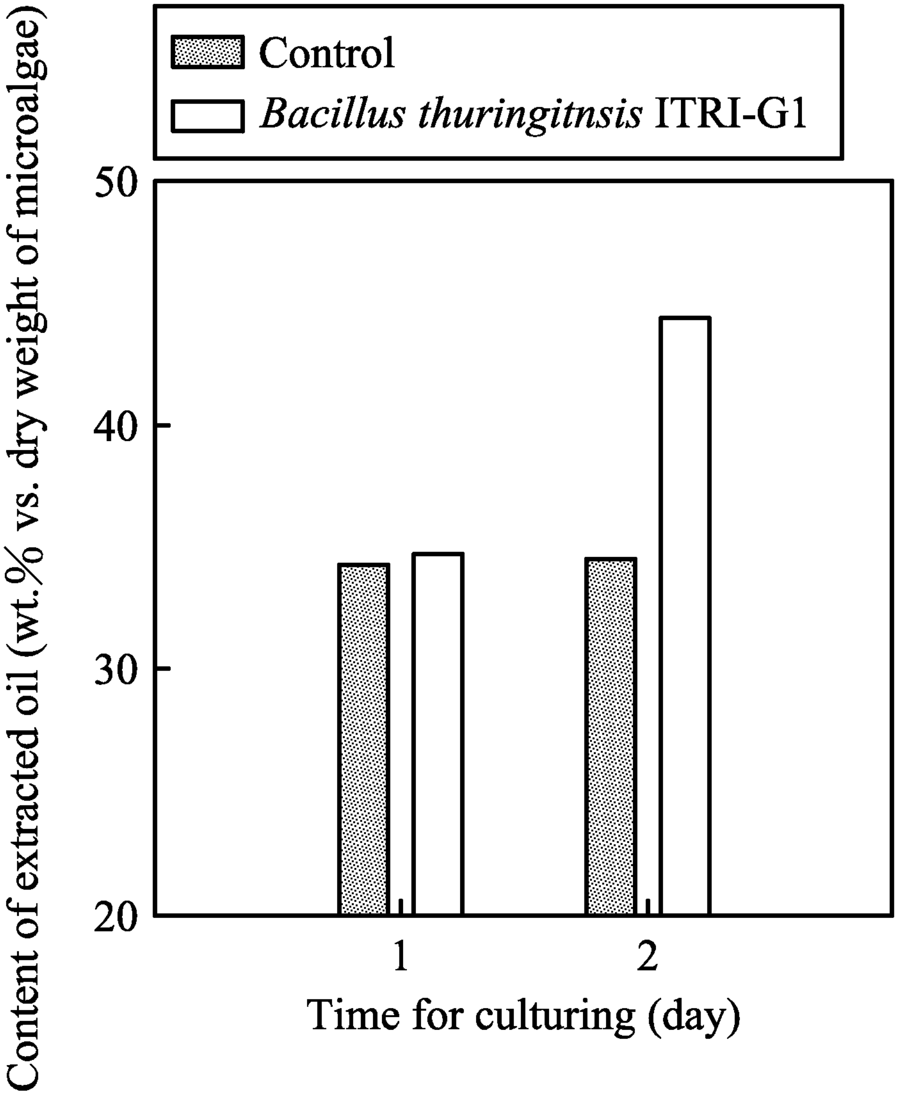
FIG. 7 shows effectiveness test of the distilled solution of the cultured medium obtained from culturing bacteria for different time periods.

The effectiveness of cell disruption of the microalgae of the active substance obtained from culturing bacteria for different time period are shown in FIG. 7.

FIG. 7 shows that the distilled solution of the cultured medium obtained from culturing *Bacillus thuringiensis* ITRI-G1 for 1 day to the end of the exponential phase does not have significant cell-disruption activity while the distilled solution of the cultured medium obtained from culturing *Bacillus thuringiensis* ITRI-G1 for 2 days has significant cell-disruption activity.

Therefore, according to the foregoing, it is known that the *Bacillus thuringiensis* ITRI-G1 strain has to grow at least to a stationary phase and then is capable of secreting the active substance for inducing self-lysis in microalga cells.

Example 8

Water Content of Microalgae Which is Disrupted in Different Manners

A *Chlorella* sp. suspension in which the cells were not disrupted, a *Chlorella* sp. suspension in which the cells were disrupted through the method of Example 2 and a *Chlorella* sp. suspension in which the cells were disrupted through mechanical disruption (ball milling for 15 minutes for cell disruption) were centrifuged at 500 rpm for 15 minutes, separately, and then the water contents of the obtained algae slurries were determined. The results are shown in Table 1.

TABLE 1

Water content of microalgae which is disrupted in different manners

| | Non cell disrupt | Disrupted through the method of Example 2 | Mechanical cell disruption |
|---|---|---|---|
| Water content | 82.1% | 83.5% | 91.1% |

Table 1 shows that water content of microalgae which is disrupted through the method of Example 2 is similar to water content of microalgae which is not disrupted while the microalgae which is disrupted through mechanical disruption has higher water content.

The microalgae which are disrupted having lower water content means that the cell disruption method which is adopted can make the microalgae which are disrupted have better dehydration properties. The microalgae having good dehydration properties means that retrieving the substances released from the microalgae and the substance used for cell disruption is easy.

Therefore, according to the results shown in Table 1, it is known that compared to mechanical cell disruption, cell disruption thorough the method of Example 2 can make the microalgae which are disrupted have better dehydration property, and retrieve the substances released from the microalgae and the substance used for cell disruption easier.

Example 9

Determination of temperature and pressure ranges suitable for a vacuum distillation procedure for obtaining the active substance inducing self-lysis in microalga cells 1. Preparation of the Active Substance for Inducing Self-lysis in Microalga Cells (1) Culture of *Bacillus thuringiensis* ITRI-G1

*Bacillus thuringiensis* ITRI-G1 was cultured by the culturing medium and culturing conditions shown below.

Culturing medium: 2 g/L peptone+0.2 g/L yeast extract

Culturing conditions: Under a shaking rate of 150 rpm, culturing at 28° C. for 2 days (2) Isolation and Purification for the Active Substance for Inducing Self-Lysis in Microalga Cells After culture of *Bacillus thuringiensis* ITRI-G1 was completed, a vacuum distillation procedure was performed on the cultured medium at different temperature by different pressure, and boiling pressure of water at respective temperature was determined.

2. Cell Disruption of Microalgae and Evaluation of Threshold Pressure for Evaporation of the Active Substance.

Fresh *Chlorella* sp. was prepared to a *Chlorella* sp. suspension with a concentration of about 150 g/L. Then the distilled solution obtained by respective vacuum distillation procedures at different temperature by different pressure mentioned above was added to the *Chlorella* sp. suspension to a concentration of *Chlorella* sp. suspension of 10 g/L. Afterward, the *Chlorella* sp. suspension was left standing for 8 hours.

After that, the optical absorbance of the *Chlorella* sp. suspension treated by respective distilled solution was measured at 280 nm to estimate whether the cell walls of *Chlorella* sp. cells are disrupted or not and to further know the maximum elevation pressure (threshold of distillation pressure) of the active substance at a respective temperature. The results are shown in Table 2 and FIG. 8.

TABLE 2

| Temperature | 40° C. | 50° C. | 60° C. | 75° C. | 90° C. |
|---|---|---|---|---|---|
| Boiling pressure of water (hPa) | 65 | 105 | 175 | 245 | 430 |
| Maximum elevation pressure of the active substance (hPa) | 95 | 155 | 245 | 345 | 550 |

Figure 8:
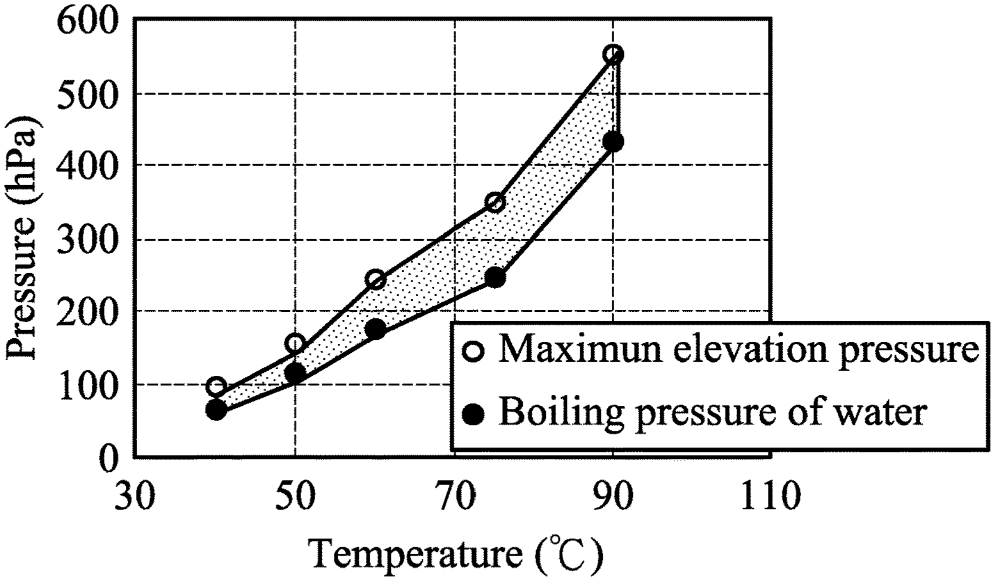
FIG. 8 shows the temperature and pressure range suitable for a vacuum distillation procedure for obtaining the active substance inducing self-lysis in microalga cells.

According to FIG. 8, it is known that temperature and pressure ranges suitable for a vacuum distillation procedure for obtaining the active substance inducing self-lysis in microalga cells is indicated by the gray region between maximum elevation pressure of the active substance and boiling pressure of water.

Example 10

High-performance liquid chromatography (HPLC) for the active substance solution

High-performance liquid chromatography was performed on the distilled solution obtained by the method of Example 2, and conditions for the high-performance liquid chromatography are shown below.

(a) Column: Jupiter® 5m C4 column (100×4.6 mm), Phenomenex;

(b) Detection wave length: 214 nm;

(c) Solvent

Solvent A: 0.1% TFA

Solvent B: 0.1% TFA+10% $CH_3CN$

Solvent C: 0.1% TFA+90% $CH_3CN$ (d) Flow rate: 1 ml/minute (f) High-performance liquid chromatography gradient program: as shown in the following Table 3.

TABLE 3

High-performance liquid chromatography

| Time (minute) | Solvent A | Solvent B | Solvent C |
|---|---|---|---|
| 0 | 100% | 0% | 0% |
| 5 | 100% | 0% | 0% |
| 7 | 0% | 100% | 0% |
| 25 | 0% | 45% | 55% |
| 27 | 0% | 0% | 100% |
| 35 | 0% | 0% | 100% |

Figure 9:
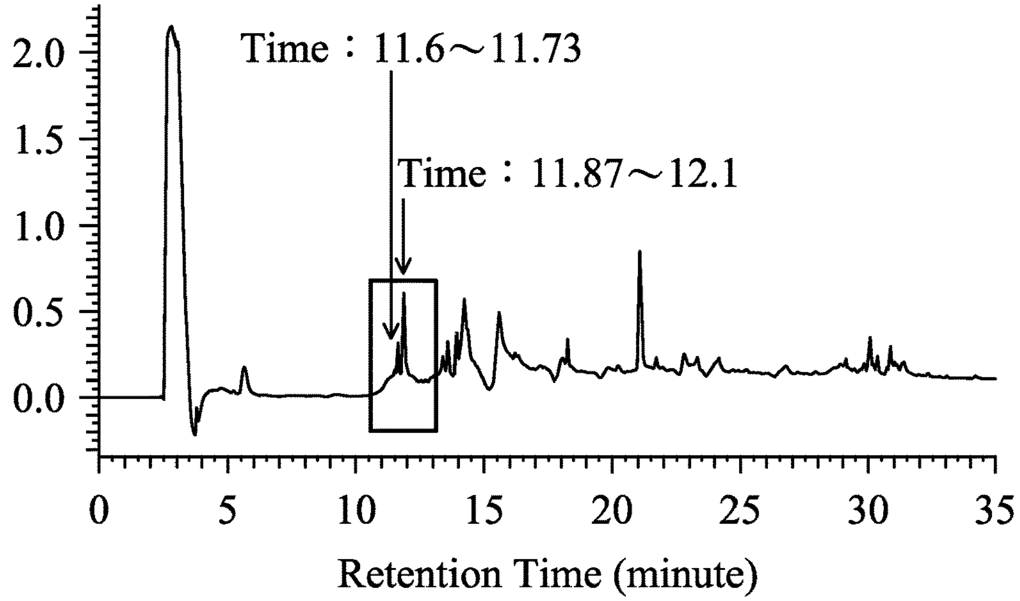
FIG. 9 shows the high-performance liquid chromatography result for the active solution of the present disclosure.

After that, a product of respective fraction (different time point) obtained from the high-performance liquid chromatography was collected. Furthermore, the result of the high-performance liquid chromatography for the active solution is shown in FIG. 9.

(2) Determination of the Fraction Product in Which the Active Substance Exists

The product of respective fraction mentioned above was added to a *Chlorella* sp. suspension (addition concentration: about 10 wt %), and the *Chlorella* sp. Suspension was left standing for 8 hours.

After that, the optical absorbance of the *Chlorella* sp. suspension treated by respective distilled solution was measured at 280 nm to estimate whether the cell walls of *Chlorella* sp. cells are disrupted or not and to determine the fraction product in which the active substance exists. The results show that the active substance exists in the fraction product between the 11.5-minute mark and the 13-minute mark (black rectangle frame region shown in FIG. 9).

Example 11

Gas Chromatography-mass Spectrometry (GC-MS) for the Active Substance

The fraction product between the 11.5-minute mark and the 13-minute mark having cell disruption activity (black rectangle frame region shown in FIG. 9) obtained from the high-performance liquid chromatography was heated at 60° C. and solid phase microextraction (SPME) (DVB/CAR/PDMS fibers were obtained from Supelco (Bellefonte, Pa., USA)) was performed thereon.

After that, gas chromatography-mass spectrometry was performed on the product of solid phase microextraction. Conditions for the gas chromatography-mass spectrometry are shown below.

Agilent 6890 gas chromatograph

Polar bonded phase BPX-5 fused silica capillary column, 25 m long, 0.22 mm I.D., film thickness 0.25 μm (SGE, Melbourne, Australia)

EI interfaced to a Agilent 5973 quadrupole mass spectrometer

NIST 11 Spectra library.

The temperature of column was programmed from 50° C. (1 minute hold) at 15° C./minute to 250° C. (5 minutes hold).

Helium was used as the carrier gas with constant flow rate at 0.6 ml/min.

The temperature of the splitless injector was 270° C. The transfer line temperature was 250° C. . The ion source and quadrupole temperature was kept at 230° C. and 150° C.

The ionization occurred with a kinetic energy of the impacting electrons of 70 eV. Mass spectra were obtained by automatic scanning in the mass range m/z 10-600.

Figure 10A:
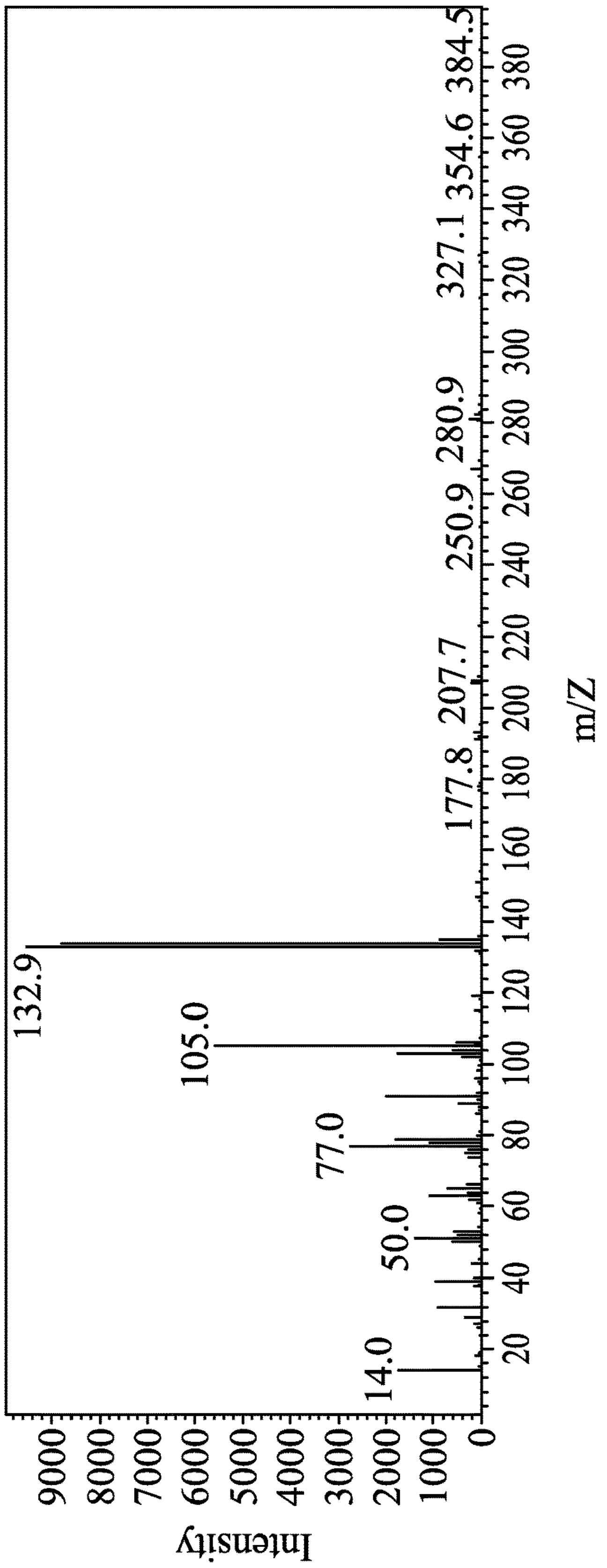
FIG. 10A shows the mass spectrometry result for the sample at the 5.9-minute mark from performing a gas chromatography on the fraction product having cell disruption activity obtained from the high-performance liquid chromatography.
Figure 10B:
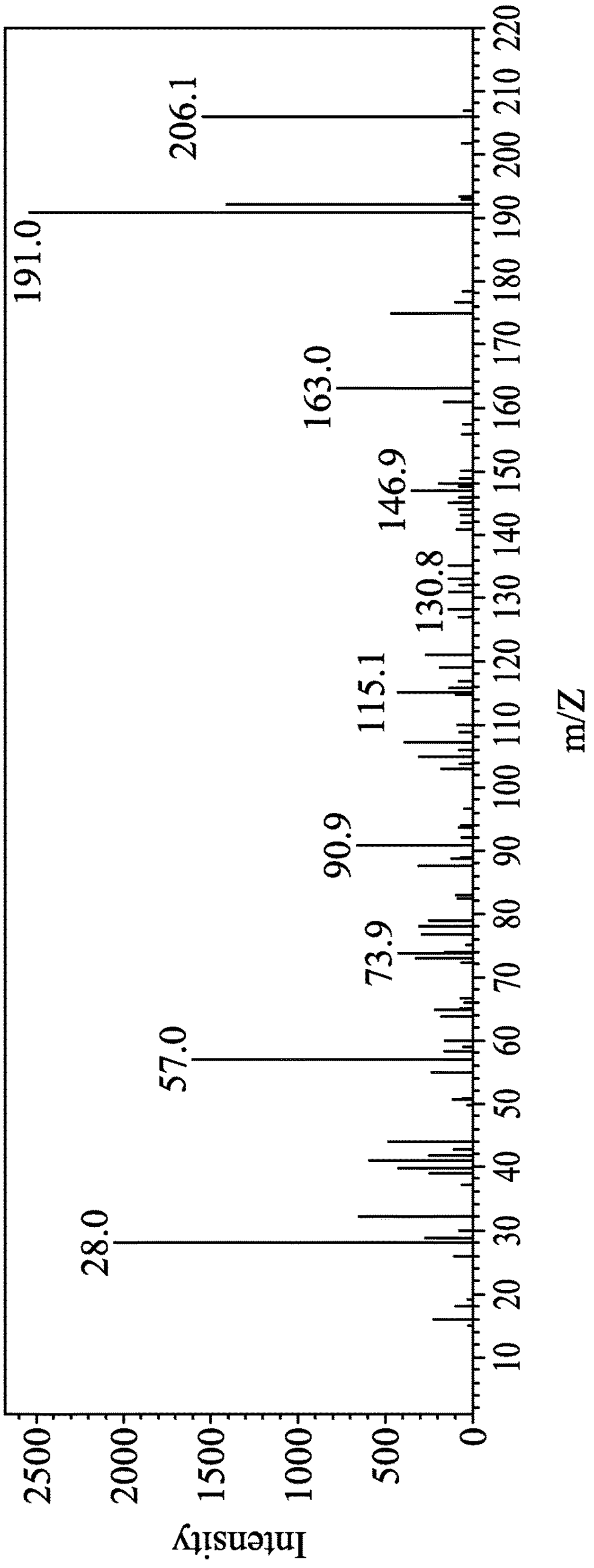
FIG. 10B shows the mass spectrometry result for the sample at the 8.5-minute mark from performing a gas chromatography on the fraction product having cell disruption activity obtained from the high-performance liquid chromatography.

The gas chromatography was performed on the fraction product having cell disruption activity obtained from the high-performance liquid chromatography mentioned above, and at the 5.9-minute mark and the 8.5-minute mark, respective substances which are probably related to cell disruption activity were obtained. Next, mass spectrometry was performed on the respective substances which are probably related to cell disruption activity obtained at the 5.9-minute mark and the 8.5-minute mark mentioned above, and the mass spectrometry results thereof are shown in FIG. 10A and FIG. 10B, respectively.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A method for manufacturing an active solution for inducing self-lysis in microalga cells, comprising:

inoculating a bacterial strain belonging to *Bacillus* into a culturing medium to obtain a bacterial suspension, wherein the bacterial strain belonging to *Bacillus* is *Bacillus thuringiensis* ITRI-G1 deposited in the German Collection of Microorganisms and Cell Cultures (DSMZ) on Dec. 11, 2014, under Accession number DSM 29807;

culturing the bacterial strain belonging to *Bacillus* at least to a stationary phase to a condition in which the bacterial strain belonging to *Bacillus* aggregates in the bacterial suspension and the bacterial suspension becomes pellucid; and after the bacterial strain belonging to *Bacillus* aggregates in the bacterial suspension and the bacterial suspension becomes pellucid, performing a vacuum distillation procedure on the bacterial suspension to obtain a distilled solution as an active solution, wherein a distillation temperature in the vacuum distillation procedure is about 40° C. and a pressure in the vacuum distillation procedure is about 65-95 hPa, or a distillation temperature in the vacuum distillation procedure is about 50° C. and a pressure in the vacuum distillation procedure is about 105-155 hPa, or a distillation temperature in the vacuum distillation procedure is about 60° C. and a pressure in the vacuum distillation procedure is about 175-245 hPa, or a distillation temperature in the vacuum distillation procedure is about 75° C. and a pressure in the vacuum distillation procedure is about 245-345 hPa, or a distillation temperature in the vacuum distillation procedure is about 90° C. and a pressure in the vacuum distillation procedure is about 430-550 hPa, and wherein the active solution is capable of inducing self-lysis in microalga cells.

2. The method for manufacturing an active solution for inducing self-lysis in microalga cells as claimed in claim 1, wherein a composition of the culturing medium comprises peptone and yeast extract.

3. The method for manufacturing an active solution for inducing self-lysis in microalga cells as claimed in claim 1, wherein the bacterial strain belonging to *Bacillus* in the bacterial suspension is cultured for 2-3 days at least to a stationary phase.

4. The method for manufacturing an active solution for inducing self-lysis in microalga cells as claimed in claim 1, wherein a temperature for culturing the bacterial strain belonging to *Bacillus* is about 20-40° C.

5. The method for manufacturing an active solution for inducing self-lysis in microalga cells as claimed in claim 1, further comprising isolating the active substance for inducing self-lysis in microalga cells from the active solution through a high-performance liquid chromatography.

6. The method for manufacturing an active solution for inducing self-lysis in microalga cells as claimed in claim 1, further comprising heating the active solution to prevent the active substance for inducing self-lysis in microalga cells therein to aggregate and decrease activity.

7. The method for manufacturing an active solution for inducing self-lysis in microalga cells as claimed in claim 6, wherein a temperature for heating the active solution is about 50-90° C.

8. The method for manufacturing an active solution for inducing self-lysis in microalga cells as claimed in claim 6, wherein time for heating the active solution is about 2-10 hours.

9. A method for inducing self-lysis in microalga cells, comprising:

inoculating a bacterial strain comprising *Bacillus thuringiensis* ITRI-G1 into a culturing medium to obtain a bacterial suspension;

culturing the bacterial strain belonging to *Bacillus* at least to a stationary phase; after the bacterial strain belonging to *Bacillus* aggregates in the bacterial suspension and the bacterial suspension becomes pellucid, taking the bacterial suspension;

performing a vacuum distillation procedure on the bacterial suspension which is taken to obtain an active solution, wherein the active solution contains an active substance for inducing self-lysis in microalga cells;

mixing microalga cells with the active solution to form a mixture solution; and letting the mixture solution stand to make the microalga cells self-lyse and precipitate.

10. The method for inducing self-lysis in microalga cells as claimed in claim 9, wherein a composition of the culturing medium comprises peptone and yeast extract.

11. The method for inducing self-lysis in microalga cells as claimed in claim 9, wherein culturing the bacterial strain belonging to *Bacillus* in the bacterial suspension for 2-3 days at least to a stationary phase.

12. The method for inducing self-lysis in microalga cells as claimed in claim 9, wherein a temperature for culturing the bacterial strain belonging to *Bacillus* is about 20-40° C.

13. The method for inducing self-lysis in microalga cells as claimed in claim 9, wherein a pressure in the vacuum distillation procedure is about 65-550 hPa.

14. The method for inducing self-lysis in microalga cells as claimed in claim 9, wherein the microalga cells account for about 4-50 wt % of the mixture solution.

15. The method for inducing self-lysis in microalga cells as claimed in claim 9, wherein the mixture solution is left to stand for about 5-30 hours.

16. The method for inducing self-lysis in microalga cells as claimed in claim 9, wherein the mixture solution is left to stand at a room temperature.

17. The method for inducing self-lysis in microalga cells as claimed in claim 9, further comprising before mixing the microalga cells with the active solution, previously heating the active solution to prevent the active substance for inducing self-lysis in microalga cells therein to aggregate and decrease activity.

18. The method for inducing self-lysis in microalga cells as claimed in claim 17, wherein a temperature for heating the active solution is about 50-90° C., and time for heating the active solution is about 2-10 hours.

19. The method for inducing self-lysis in microalga cells as claimed in claim 9, further comprising after the microalga cells precipitate, retrieving a supernatant of the mixture solution to retrieve the active substance for inducing self-lysis in microalga cells in the supernatant.

20. The method for inducing self-lysis in microalga cells as claimed in claim 19, further comprising heating the supernatant to prevent the active substance for inducing self-lysis in microalga cells therein to aggregate and decrease activity.

21. The method for inducing self-lysis in microalga cells as claimed in claim 20, wherein a temperature for heating the supernatant is about 50-90° C., and time for heating the supernatant is about 2-10 hours.

22. The method for inducing self-lysis in microalga cells as claimed in claim 9, wherein the microalga cells are unicellular algae microorganisms having cell wall shells for protection.

23. The method for inducing self-lysis in microalga cells as claimed in claim 9, wherein the microalga cells are microalga cells in a condition of being fresh and alive.

24. The method for inducing self-lysis in microalga cells as claimed in claim 9, wherein the microalga cells comprise *Chlorella* sp., *Micractinium* sp., *Nannochloropsis* sp., *Tetraselmis* sp., *Isochrysis galbana* or *Dunaliella* sp.

* * * * *